(12) United States Patent
Flyash et al.

(10) Patent No.: US 8,606,366 B2
(45) Date of Patent: Dec. 10, 2013

(54) SKIN TREATMENT APPARATUS FOR PERSONAL USE AND METHOD FOR USING SAME

(75) Inventors: Lion Flyash, Nazareth Illit (IL); Boris Vaynberg, Zikron Yaakov (IL)

(73) Assignee: Syneron Medical Ltd., Yoqneam Illit (IL)

( * ) Notice: Subject to any disclaimer, the term of this patent is extended or adjusted under 35 U.S.C. 154(b) by 884 days.

(21) Appl. No.: 12/388,309

(22) Filed: Feb. 18, 2009

(65) Prior Publication Data
US 2010/0210993 A1 Aug. 19, 2010

(51) Int. Cl.
*A61F 7/00* (2006.01)
*A61F 7/12* (2006.01)

(52) U.S. Cl.
USPC .......................................................... 607/98

(58) Field of Classification Search
USPC .......... 604/20; 607/98, 99, 101, 150, 147, 13, 607/20–22, 2, 3
See application file for complete search history.

(56) References Cited

U.S. PATENT DOCUMENTS

| 6,889,090 B2* | 5/2005 | Kreindel ........................ 607/101 |
| 8,135,475 B2* | 3/2012 | Kreindel et al. ................. 607/99 |
| 2002/0082543 A1* | 6/2002 | Park et al. ........................ 604/21 |

FOREIGN PATENT DOCUMENTS

WO   WO 2006/128034 A1 * 11/2006

* cited by examiner

*Primary Examiner* — Nicholas Lucchesi
*Assistant Examiner* — Pritesh Patel
(74) *Attorney, Agent, or Firm* — Smith Risley Tempel Santos LLC; Gregory Scott Smith

(57) ABSTRACT

An apparatus for personal skin treatment includes an RF generator and an applicator with at least a pair of electrodes mounted on the distal end of the applicator. The electrodes are configured for applying an RF voltage to a subject skin. The RF voltage generator supplies the electrodes with the RF voltage. The applicator includes a source of illumination illuminating the treated skin segment.

13 Claims, 15 Drawing Sheets

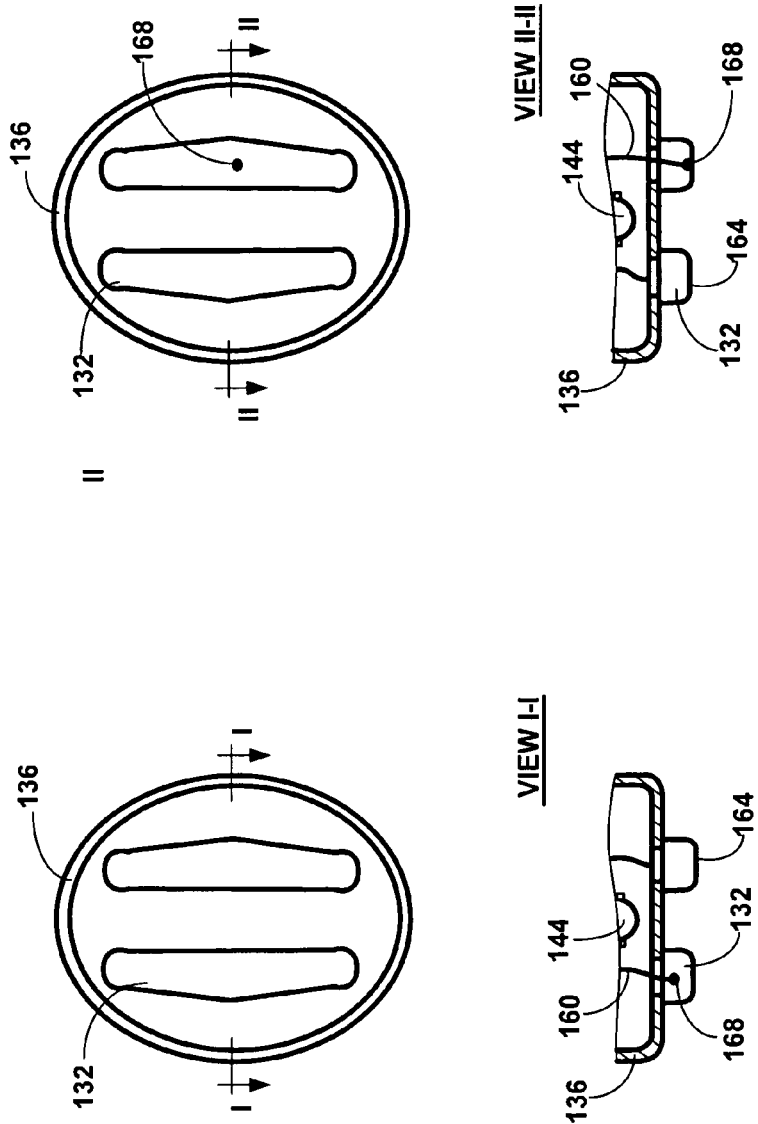

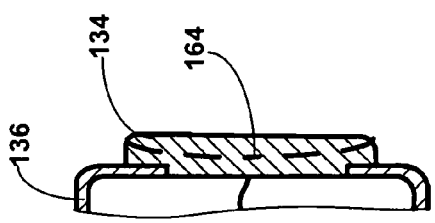
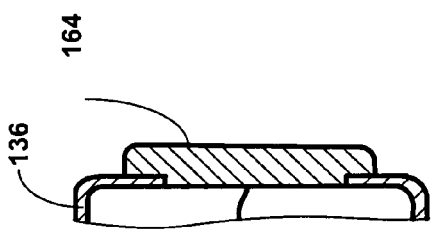
FIG. 5B
FIG. 5A

US 8,606,366 B2

SKIN TREATMENT APPARATUS FOR PERSONAL USE AND METHOD FOR USING SAME

TECHNOLOGY FIELD

The method and apparatus are related to the field of personal cosmetic procedures and in particular to wrinkle removal procedures.

BACKGROUND

External appearance is important to most people. In recent years, methods and apparatuses have been developed for different cosmetic treatments. Among these are hair removal, treatment of vascular lesions and skin rejuvenation. In these treatments, a volume of skin tissue under the skin is heated to a temperature that is sufficiently high as to achieve a desired skin effect. The temperature producing the desired effect is typically in the range of 38-60 degrees Celsius. One method that has been used for heating the epidermal and dermal layers of the skin is pulsed or continuous radio-frequency (RF) energy. In this method, electrodes are applied to the skin and an RF voltage pulse is applied across the electrodes. The properties of the voltage pulse are selected so as to generate an RF current pulse which heats the tissue to the required temperature.

Presently, a number of light based skin surface or deeper skin layer treatments have been developed. These treatments typically use laser diodes, LED, Xenon lamp (Intense Pulsed Light or IPL) or incandescent lamp radiation to irradiate a surface of skin where vascular lesions, varicose veins, acne, mole marks and similar disorders are present. The optical radiation may have a single wavelength or several wavelengths. The wavelengths are selected to be optimal for the color of the contrasted component of the target skin segment, and are typically in the range of 400 to 1800 nm.

The above described equipment is both costly and bulky. It is typically operated in an ambulatory set-up by a qualified operator and frequently requires the presence of medical personnel specialized in such treatments. There is a need on the market for a small size, low cost, and safe to use apparatus that may be operated by the user and enable the user to use the equipment and get results similar or identical to those achieved by professional equipment skin treatments.

BRIEF SUMMARY

An apparatus for personal cosmetic skin treatment including an RF generator and an applicator with at least a pair of electrodes mounted on the distal end of the applicator. The electrodes are configured for applying an RF voltage to a subject skin. The RF generator is configured to supply a number of RF voltage types to the electrodes. A source of light is arranged between electrodes and illuminates the skin segment between the electrodes. The applicator is moved over the skin in a scanning movement applying RF voltage to the segment of skin between the electrodes. The source of light operates concurrently or sequentially with the RF generator and illuminates the same segment of skin.

BRIEF LIST OF DRAWINGS

The apparatus and the method are particularly pointed out and distinctly claimed in the concluding portion of the specification. The apparatus and the method, however, both as to organization and method of operation, may best be understood by reference to the following detailed description when read with the accompanying drawings, in which like reference characters refer to the same parts throughout the different views. The drawings are not necessarily to scale, emphasis instead being placed upon illustrating the principles of the method.

FIGS. 1A and 1B, jointly referred to as FIG. 1, are schematic illustrations of an exemplary embodiment of the apparatus for personal skin treatment.

FIGS. 4A and 4B, jointly referred to as FIG. 4, are schematic illustrations of some exemplary electrode-thermocouple configurations of the applicator.

Figure 5C:
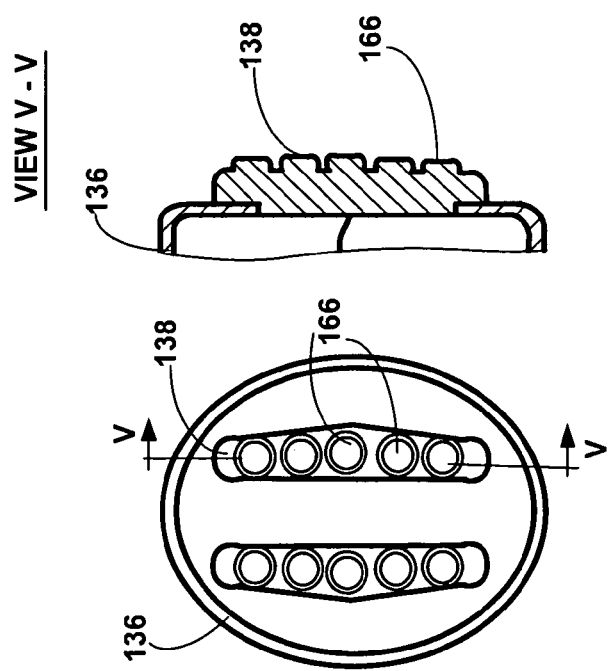

FIGS. 5A, 5B and 5C, jointly referred to as FIG. 5, are schematic illustrations of some additional exemplary applicator electrode configurations.

Figure 6:
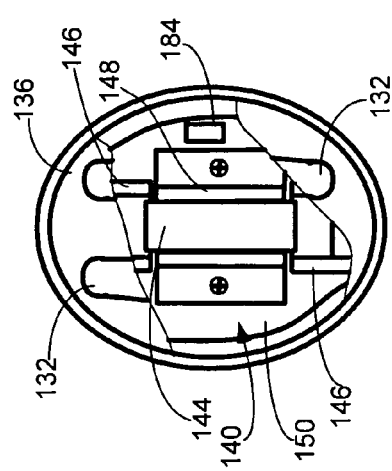

FIG. 6 is a schematic illustration of a cross section of the applicator of FIG. 1 in plane perpendicular to longitudinal axis of the applicator.

Figure 7:
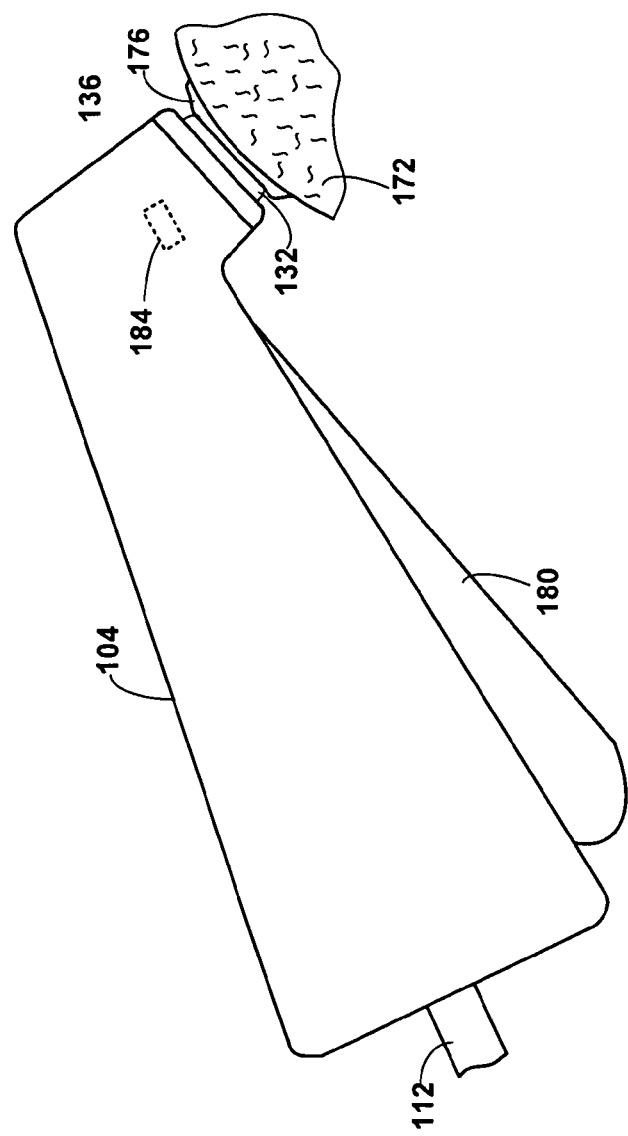

FIG. 7 is a schematic illustration of an applicator with a built-in gel dispenser.

Figure 8:
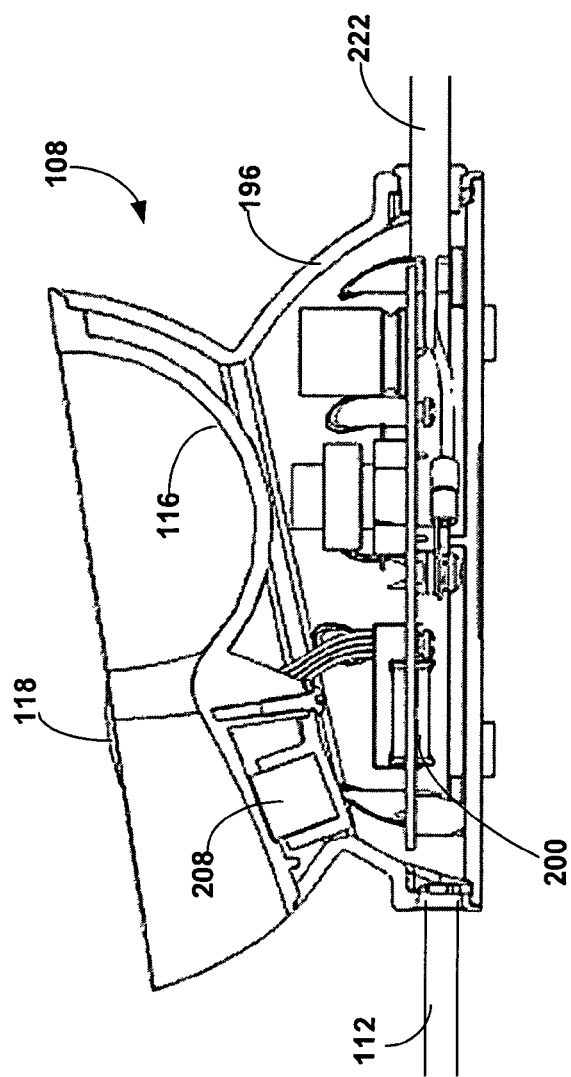

FIG. 8 is a schematic illustration of a cross section of the docking stand of the apparatus for skin treatment.

Figure 9:
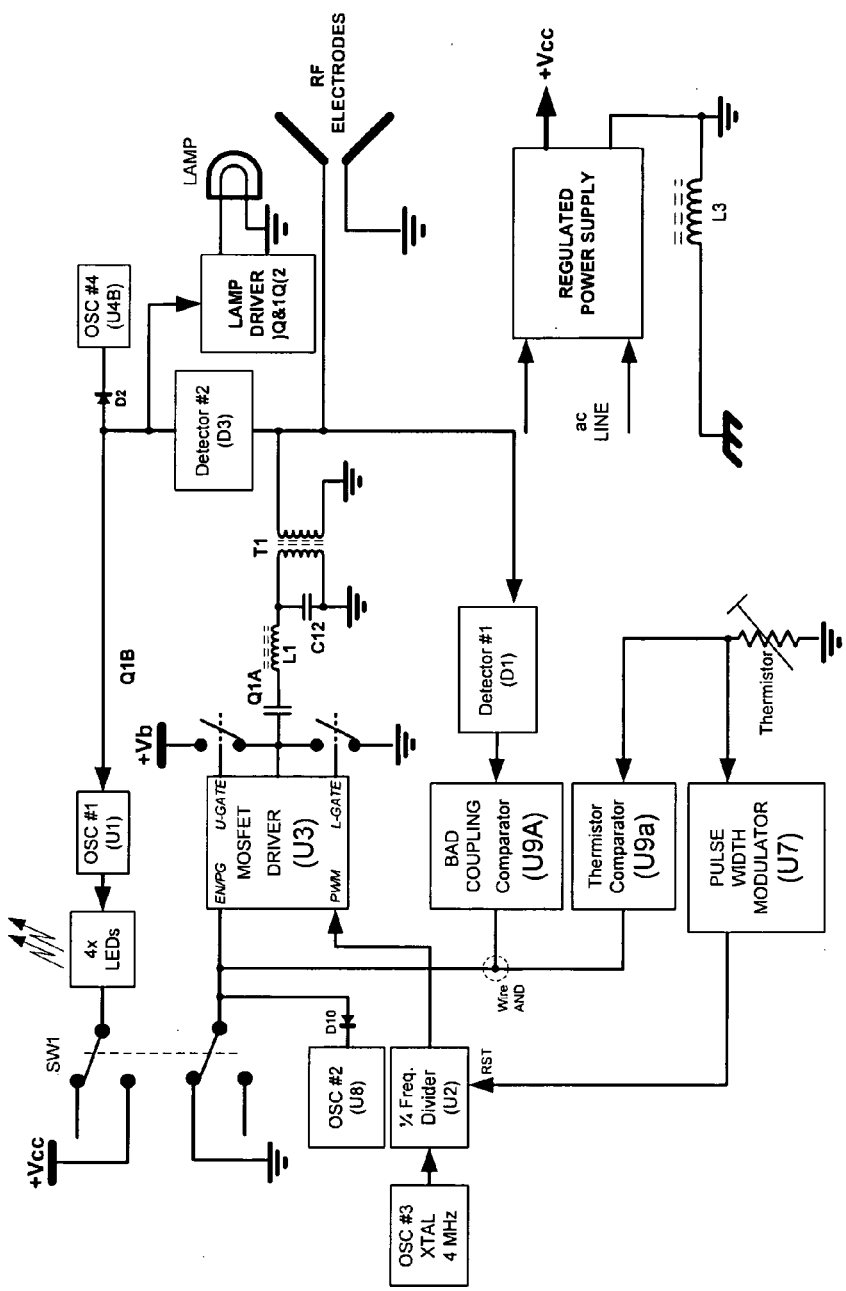

FIG. 9 is a schematic illustration of an exemplary embodiment of the electronic circuit of the apparatus for skin treatment.

Figure 10:
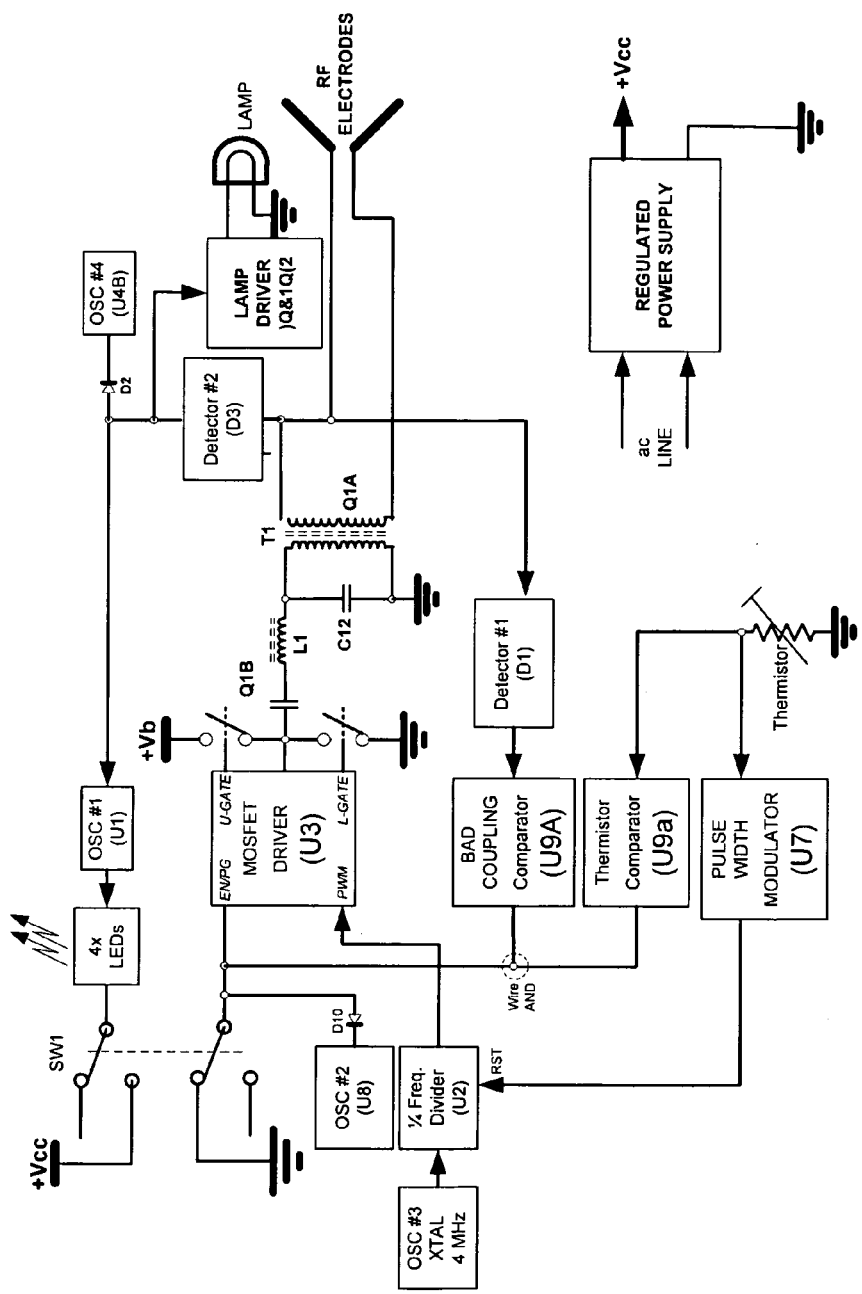

FIG. 10 is a schematic illustration of another exemplary embodiment of the electronic circuit of the apparatus for skin treatment.

Figure 11:
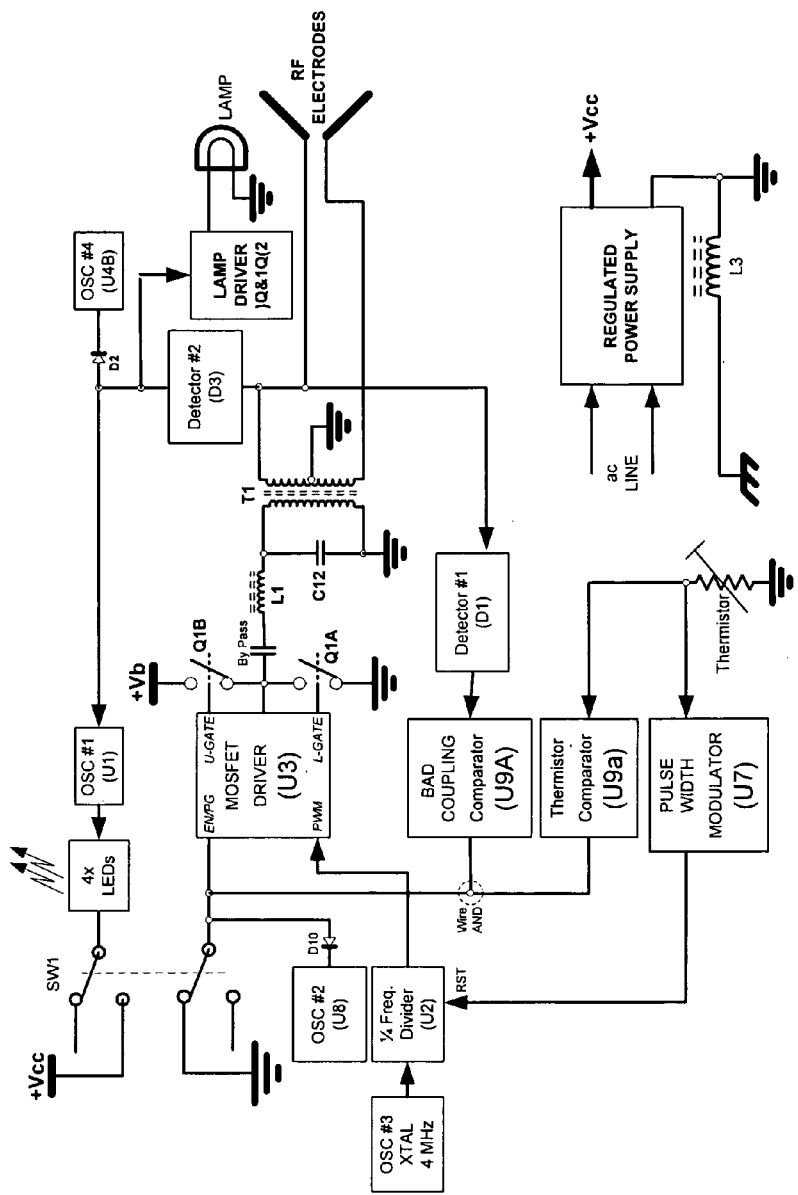

FIG. 11 is a schematic illustration of an additional exemplary embodiment of the electronic circuit of the apparatus for skin treatment.

Figure 12:
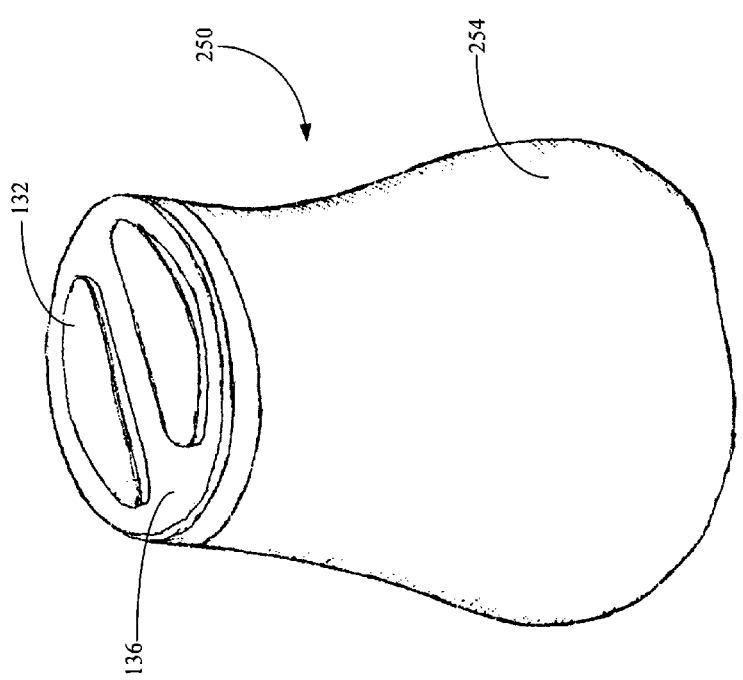

FIG. 12 is a schematic illustration of an additional embodiment of the apparatus for personal skin treatment.

Figure 13:
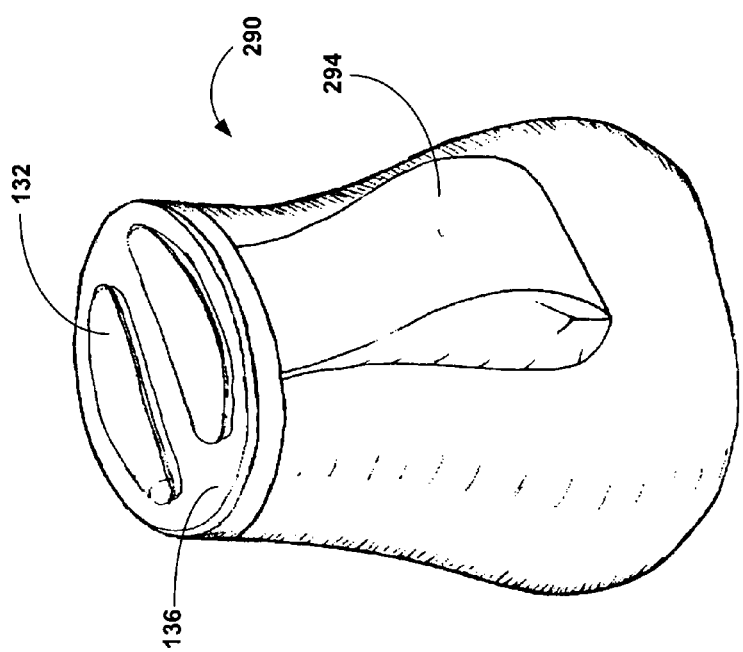

FIG. 13 is a schematic illustration of a further embodiment of an apparatus for personal skin treatment with a built-in gel dispensing arrangement.

Figure 14:
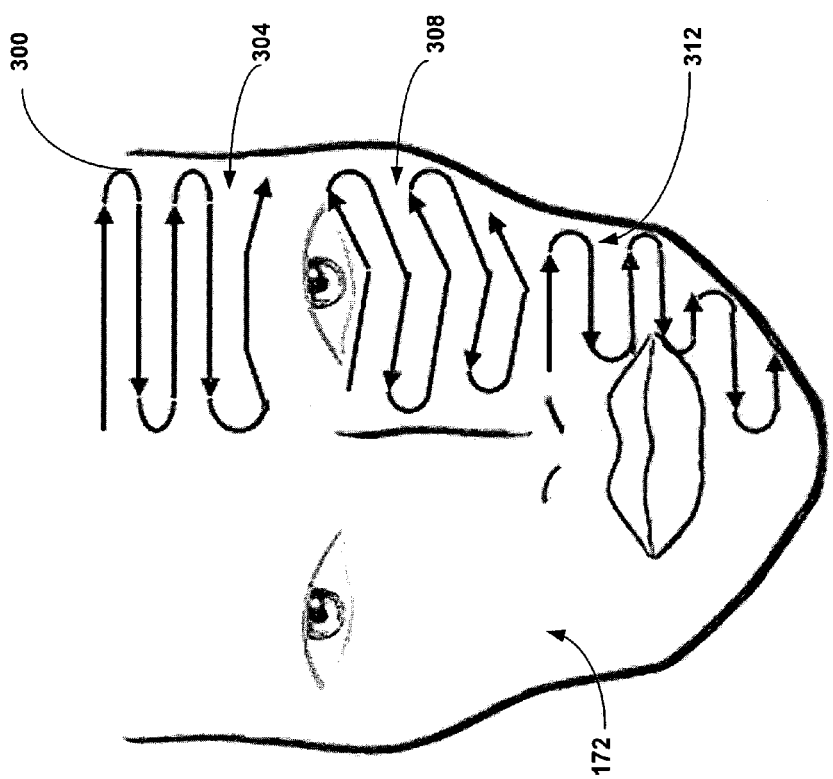

FIG. 14 is a schematic illustration of typical skin treatment scanning movements of the applicator.

DETAILED DESCRIPTION OF THE EXEMPLARY EMBODIMENTS

In the following detailed description, reference is made to the accompanying drawings which form a part hereof. This is shown by way of illustrating different embodiments in which the apparatus and method may be practiced. Because components of embodiments of the present apparatus can be positioned in a number of different orientations, the directional terminology is used for purposes of illustration and is in no way limiting. It is to be understood that other embodiments may be utilized and structural or logical changes may be made without departing from the scope of the present method and apparatus. The following detailed description, therefore, is not to be taken in a limiting sense, and the scope of the present apparatus and method is defined by the appended claims.

As used herein, the term "skin treatment" includes cosmetic skin treatment of various skin layers such as stratum corneum, dermis, epidermis, skin rejuvenation procedures, wrinkle removal, and such procedures as collagen shrinking or destruction. The term "skin surface" relates to the most external skin layer, which may be stratum corneum.

Figure 1A:
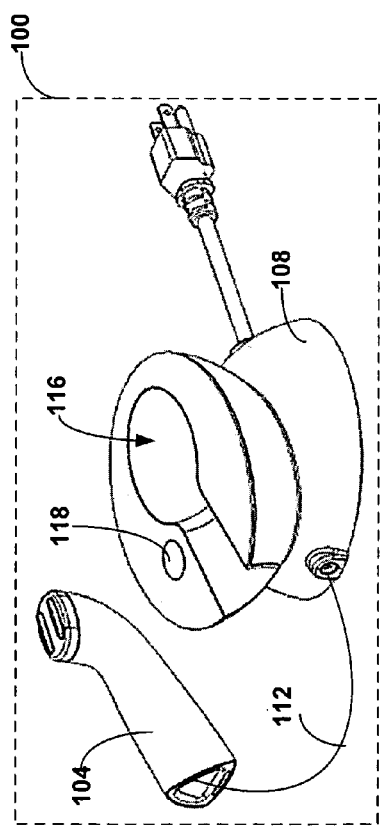
Figure 1B:
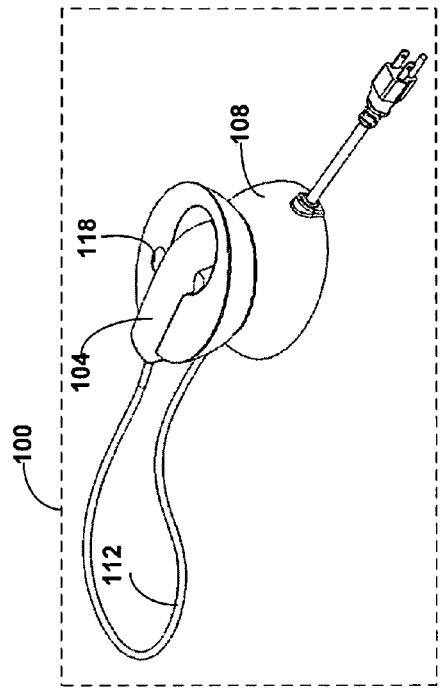

Reference is made to FIG. 1, which is a schematic illustration of an exemplary embodiment of the apparatus for personal skin treatment. Apparatus 100 (FIG. 1A) comprises an applicator 104 adapted for sliding movement on a subject skin, a docking stand 108 on which the applicator is placed when not in use (FIG. 1B) and harness 112 connecting applicator 104 and stand 108. Harness 112 enables electric or other type of communication between applicator 104 and stand 108. When not in operation, applicator 104 may be located in a docking bay 116 (FIG. 1B) of stand 108. Apparatus 100 may receive power supply from a regular electric supply network receptacle, or from a rechargeable or regular battery. Lamp 118 indicates operational status of stand 108.

Figure 2:
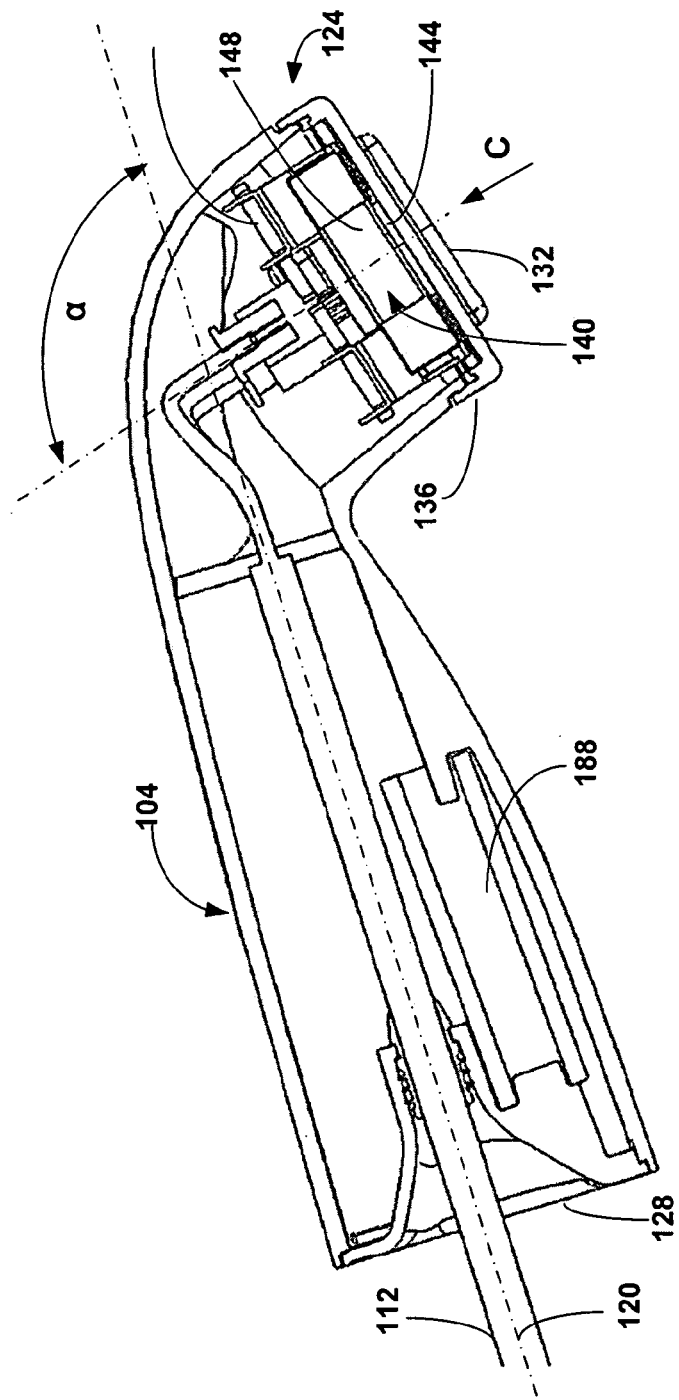
FIG. 2 is a schematic illustration of a cross section along the longitudinal axis of an exemplary embodiment of the applicator of the apparatus of FIG. 1.

FIG. 2 is a schematic illustration of a cross section along the longitudinal axis of the applicator of the present apparatus. Applicator 104 is shown to have body or handle, ergonomically shaped or suitably shaped for holding with the hand, and having a longitudinal axis 120 with extending and projecting forward distal end 124 and a proximal end 128. Distal end 124 is typically oriented at an angle α degrees to axis 120. Angle α is selected to enable proper contacts between electrodes 132 and a target area of skin or material to be treated, and at an angle to facilitate convenience in holding applicator 104. For instance, the angle α may be about 110 degrees. Mounted on distal end 124 of the applicator 104 are one or more RF applying electrodes 132 connected through harness 112 to a source of RF voltage (not shown) located in stand 108. An optical filter 136 serves as a mounting basis for electrode 132. Optical filter 136 also serves as an operation indicator of applicator 104. Optical filter 136 is typically a broadband glass or plastic filter that transmits red and infrared wavelength and typically lights with a reddish or first color.

Mounted at the distal end 124 of applicator 104 is a source of light 140 that may be an incandescent lamp 144 or an incandescent lamp optimized (doped) for emission of red and infrared radiation. The useful spectrum of lamp 144 may be in the range of 400 to 1800 nm and emitted optical energy in the range of 1 W to 20 W. A reflector 148 collects and directs radiation emitted by lamp 144 towards a segment of skin to be treated. Alternatively, an LED emitting one or more suitable wavelengths or a semiconductor laser may be used instead of lamp 144. When LEDs are used as radiation emitting sources their wavelengths may be selected such that one of them will serve as an operation indicator of first color canceling the need for a special filter. The remaining LEDs may provide the wavelengths required for the treatment. A single LED with multiple emitters may also be used. Shown is a magnetic or a ferromagnetic insert 188 cooperating with magnet 208 (FIG. 8) and holding applicator 104 in docking bay 116 (FIGS. 1 and 8) of stand 108.

Figure 3:
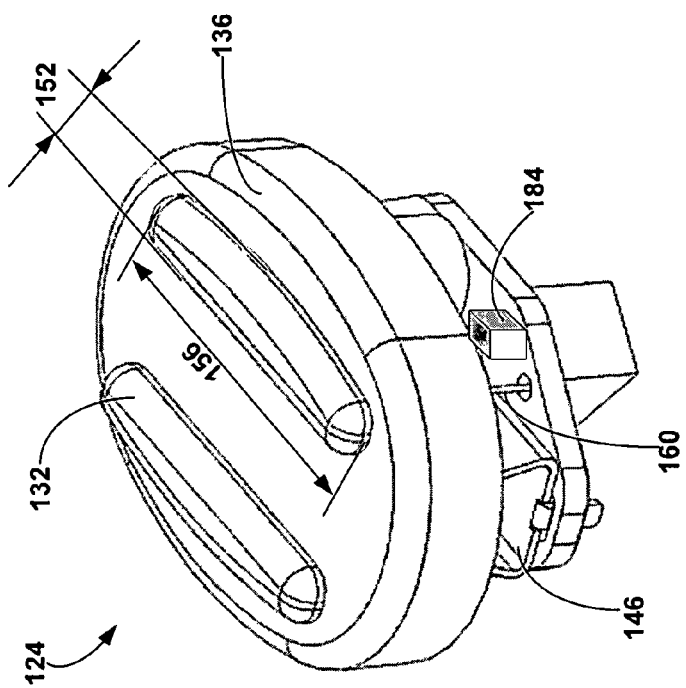
FIG. 3 is a schematic three-dimensional illustration of an exemplary embodiment of a distal end of the applicator.

FIG. 3 is a schematic three-dimensional illustration of an exemplary embodiment of the distal end 124 of applicator 104. FIG. 3 illustrates electrodes 132 mounted on filter 136, thermocouple 160 built-in into at least one of the electrodes 132, and lamp holder 146. Electrodes 132 typically have an elongated body with width 152 to length 156 ratio of at least 1:5. The geometry of the electrodes is optimized to selectively heat the skin in the area between the electrodes. Electrodes 132 typically have rounded edges in order to avoid hot spots on the skin surface near the edges of the electrodes. Rounded electrodes also allow smooth movement of applicator 104 (FIG. 1) over the skin surface. FIG. 3 illustrates a bi-polar electrode system, although a uni-polar electrode system (not shown) may be used. Alternatively, when more than one electrode 132 is used the bi-polar or uni-polar system may be generated by feeding a proper RF voltage to the electrodes.

FIG. 4 is a schematic illustration of some electrode-thermocouple configurations of the applicator. In the embodiment illustrated in FIG. 4A, one or more electrodes 132 may have a built-in thermocouple 160 residing with the temperature-sensing end 168 inside electrode body 132. In another embodiment, shown in FIG. 4B, the temperature-sensing end 168 of thermocouple 160 may be flush with electrode 132 contacting skin surface 164. In some embodiments a thermistor may be used instead of the thermocouple. The thermistor may be embedded into one or more electrodes, or as a standalone probe being in contact with the treated skin segment. Thermocouple 160 having a temperature sensing end flush with electrode 132 surface 164 measures skin temperature, where residing within electrode 132 end of thermocouple 160 measures only electrode 132 temperature. Thermocouple 160 communicates the measured temperature to a feedback loop of RF voltage generator 200 (FIG. 8). Based on temperature values, RF voltage generator 200 may increase or decrease RF voltage amplitude, change the duty cycle of the RF voltage supplied to electrodes 132, or even switch off the RF voltage generator.

FIG. 5 is a schematic illustration of some electrode configurations of applicator 104. In one embodiment (FIG. 5A), electrode 132 is a solid electric current conducting body. In another embodiment (FIG. 5B), electrode 134 may be a flexible electric current conducting body. A flexible electrode is capable of adapting its shape to the contours of the treated subject skin enabling a better contact with the skin. In an additional embodiment (FIG. 5C), electrode 138 may have a relief 166 on the skin contacting surface 164. The relief may be a plurality of microelectrodes or a plurality of macro electrodes.

FIG. 6 is a schematic illustration of a cross section of the applicator of FIG. 1 in plane perpendicular to longitudinal axis of the applicator. It further demonstrates the construction of light source 140. Lamp 144 and reflector 148 are located between electrodes 132. Filter 136 protects lamp 144 and cuts out of the lamp emission a desired spectral range out of a spectrum emitted by lamp 144. The listed elements are assembled on a type of printed circuit board support 150. The illustrated embodiment also shows the inclusion of an optional accelerometer 184.

In order to improve the coupling of RF induced current to the skin 172 (see FIG. 7) it is desirable to cover skin 172 by a layer of gel 176 improving electric contact between electrodes 132 and skin 172 and facilitating electrode on skin gliding. Typically, gel 176 is dispensed over skin 172 before the treatment, and remains on the skin during the treatment. Gel dispensing, in addition to skin cleaning performed by water and soap or other cleaning means, represents a skin pretreatment operation. According to one embodiment, gel 176 may be dispensed manually. A disposable flexible container actuated manually by the user squeezes and dispenses gel 176 over skin 172. In a further embodiment, gel dispenser 180 may be a part of applicator 104 and is actuated automatically during treatment from a disposable or refillable container. Alternatively, gel dispenser may be located in stand 108. Where gel dispenser is located in stand 108, harness 112 (FIG. 1) in addition to electrical lines may contain a suitable tubing for supplying gel 176 to distal end 124 of applicator 104 and skin 172. In order to enable good contact and facilitate the treatment gel 172 may have an electrical resistance higher than the skin being treated.

Applicator 104 may include an accelerometer 184, similar to the accelerometer of FIG. 6, which could detect and provide an indication of the movement of applicator 104 and the speed of the movement. Accelerometer 184 communicates with RF voltage generator 200 (see FIG. 8). Based on the changes in the speed of advance (acceleration) of applicator 104, RF voltage generator 200 may increase or decrease RF voltage amplitude or change the duty cycle of the RF voltage supplied to electrodes 132, enabling optimal maintenance of the treatment temperature.

FIG. 8 is a schematic illustration of a cross section of the docking stand of the apparatus for providing skin treatment. Stand 108 may be an aesthetic looking plastic or metal enclosure 196 incorporating an RF voltage generator 200, an operation indicator 118, and a permanent or electric magnet 208 for holding or securing the applicator 104 with in the docking stand at a particular position. In some embodiments, the RF voltage generator may be located in the applicator 104. Operation indicator 118 may be a lamp similar to lamp 118 having a second color different from the first color of lamp 144. Operation indicator 118 may also serve as a stand-by mode indicator. The lamp or a LED providing the second color may be greenish or bluish. A glass or plastic filter may be used so that a simple incandescent lamp can be used as an indicator. Stand 108 may receive power supply from a regular electric network receptacle with the help of power cord 222 or be equipped by rechargeable batteries.

RF voltage generator 200 has at least one feedback loop operated by a signal received from thermocouple 160 (see FIG. 4). The same or an additional feedback loop may be operated, as explained above, by a signal provided by accelerometer 184 (see FIG. 3 and FIG. 6). Alternatively, the impedance of the treated skin segment may be monitored and used for Automatic RF Power Control (APC). It is known that RF generator output depends on the load. It is desirable to maintain the load flat or uniform during operation. This is, however, possible only in a certain range of treated skin impedance and it may be desirable to operate apparatus 100 in a mode that minimizes skin impedance changes. It is also known that skin parameters vary widely between different treated subjects. A typical range of impedance changes may be from 50 to 400 ohm. (It is necessary to mention that electrode configuration may affect impedance range.) Even for the same person, the impedance of the skin located proximate to the forehead and cheek may be substantially different. The type of contact between the electrodes and skin also affects impedance value. An electrode may contact the skin with its entire surface or only partially, depending on skin relief of the face segment. The feedback loops, and in particular the impedance-based loop, allows constant RF power output to be maintained for all the range of skin impedances. Practically, the impedance of the treated skin segment is constantly monitored and the RF power is adjusted accordingly.

FIG. 9 is a schematic illustration of an exemplary embodiment of the electronic circuit of the apparatus 100 for skin treatment. Typically, the treated subject is isolated from the Earth of power supply network. When both RF electrodes are applied to the skin of the subject, the skin, being a conductor, short circuits the electrodes and provides a pass for the RF induced current. Conductive gel that has a resistance higher than the skin facilitates this current pass. In this particular implementation, one of the electrodes is connected to the ground through an inductor L3. The resulting bi-polar RF electrodes create a zero potential at one electrode while the other electrode relative to ground is at maximum potential.

FIG. 10 is a schematic illustration of another exemplary embodiment of the electronic circuit of the apparatus for skin treatment. This particular embodiment discloses a design where RF electrodes are not grounded at all. When the RF electrodes touch the subject skin, an RF current flows through the skin between the electrodes. The bipolar RF electrodes create a minimum potential between them in the middle, regardless of the potential of the subject with respect to ground.

FIG. 11 is a schematic illustration of an additional exemplary embodiment of the electronic circuit of the apparatus for skin treatment. In this case, the output RF generator stage contains a transformer with a secondary center tap connected to ground-earth through an inductor L3. This enables a zero potential to be obtained relative to ground in the middle of the span between the electrodes.

All of the above disclosed electronic schemes enable supply of the required RF power to the electrodes and avoid subject electric shock even if the subject is in contact with the Earth.

FIG. 12 is a schematic illustration of an additional embodiment of the apparatus for personal skin treatment. Apparatus 250 is a convenient-to-hold body 254 incorporating the applicator and stand elements. Apparatus 250 may be plugged into a conventional electric power supply network or be battery operated. The battery may be rechargeable. All earlier described apparatus 100 (FIG. 1) components are mutatis mutandis applicable to apparatus 250. Operation of apparatus 250 is similar to operation of apparatus 100. When the RF electrodes touch the subject skin, apparatus 250 is activated and an RF induced current flows through the skin between the electrodes. When there is no contact between the electrodes and the skin apparatus 250 is in stand-by mode. Optionally, apparatus 250 may have an ON-OFF switch to switch it off completely.

FIG. 13 is a schematic illustration of a further embodiment of an apparatus for personal skin treatment with built-in gel dispensing arrangement. According to one embodiment, apparatus 290 may have a receptacle for a disposable flexible gel container 294. The gel may be dispensed over the skin manually by application of pressure to container 294. In a further embodiment, gel dispenser (not shown) may be a part of apparatus 290 or a type of an automatic dispenser, which pulls gel required for the treatment out of a disposable or refillable container.

The method of skin treatment using the present apparatus will be explained now. Following cleaning and gel spreading over a target segment of skin 172, applicator 104 is placed over the skin segment 172 such that electrodes 132 are in contact with skin 172. Practically, the skin 172 becomes a conductor automatically closing the circuit and enabling an RF current passage between electrodes 132. Induced by RF voltage, current passes through skin 172 and heats it to a desired temperature. RF voltage is applied to electrodes 132 in a continuous or quasi-continuous mode and with duration of at least 0.5 second.

FIG. 14 is a schematic illustration of typical skin treatment scanning movements of the applicator. Applicator 104 may be moved in a type of reciprocal scanning motion as shown by arrows 300 over the skin 172 to treat next skin segment 312. In the course of movement of the applicator it maintains contact between electrodes 132 and skin 172 and delivers a continuous RF power inducing current to treated skin segments 304 - 312 located between electrodes 132.

Applicator 104 (or apparatus 250) is displaced over the skin segment to be treated so that RF induced current heats the treated skin segment to a temperature that produces the desired treatment of the skin, for example, stimulating the process of collagen remodeling in the skin. Typically, the RF power applied across electrodes 132 can range from 1 W to 20 W but, it is anticipated that other values and ranges may also be applied. The RF power is applied in a continuous or quasi-continuous mode for a period of time, such as at least 0.5 second as a non-limiting example. Applied in this mode, RF power is capable of heating skin from a normal skin temperature to a temperature of about 60 degrees Celsius. It should be noted that the typical treatment time per skin segment is based on several factors. One such factor is the characteristics of the treated skin segment. For example, a bony area with thin skin, like the forehead (segment 304) versus thicker skin in a non-bony segment, such as the area around the eyes (segment 308);. Another factor includes the average surface area per segment. For example, each cheek, jaw line and chin area (segment 312) will require more time than any of the other areas, each of which is effectively smaller than segment 312. In an exemplary treatment process it may be desirable to spend the necessary time on each treatment zone until the desirable treatment end-point is reached. The treatment end-point may be characterized among others by erythema and a significant heat sensation with possible edema and a tightening feeling. The treatment may be continued for an additional 1-2 minutes stabilizing the treatment effect.

During treatment, skin and electrode temperature sensors or acceleration sensors, or impedance monitoring provide an input to the feedback loops of RF voltage generator 200 (see FIG. 8). Based on input of at least one of the sensors feedback, the RF power automatically changes providing and maintaining optimal treatment conditions. The RF voltage changes may include amplitude changes, voltage application time changes or voltage application duty cycle changes. For example, upper and lower treatment temperature limits may be set. If the feedback indicates that the first or upper temperature limit, which may be set for skin temperature exceeding 44 degrees Celsius, automatic reduction in RF power or change of the applied RF power duty cycle may take place. The duty cycle may be reduced to 60% of the maximal operating value. A complete switch-off of the RF power at a second or upper temperature limit, for example at temperature exceeding 45 degrees Celsius may take place. The RF power may also be changed in response to changes in the scanning speed of the applicator 104 as reported or determined by signals received from accelerometer 184. Despite certain RF power reduction, the treatment may continue because, in order to get proper treatment results, it is desired not only to reach a certain temperature in the tissue, but to maintain it for some threshold period of time. To satisfy this requirement, the decrease in RF power may not exceed 30% or 40% of the maximal allowable RF power. At the reduced RF power level, the existing natural blood flow may dissipate sufficiently to affect the temperature in the skin. The second or upper temperature limit is primarily a safety limit preventing damage to the skin.

A person treating his own skin with apparatus 100 may simply displace applicator 104 (or apparatus 250) over the skin surface in the segment of skin to be treated at a reasonable speed where the temperature or acceleration feedback will adjust the RF power to obtain the desired treatment result. Known methods of monitoring the skin impedance between electrodes 132 and allowing the temperature of the skin between the electrodes to be followed by changing RF power may be also applied to the present treatment method. It is known that temperatures of about 40 degrees Celsius and lower do not cause the desired skin treatment effect. In cases where the user moves applicator 104 faster than desired, the temperature and acceleration feedback systems adjust the RF power to get a desired treatment effect. An audible signal alerting the user on the desired temperature or acceleration may be generated by a buzzer located in stand 108.

Temperature and acceleration feedback loops automatically adjust the treatment parameters to the electrical properties of the treated person's skin. These feedback loops avoid an undesired rise in temperature of the skin and limit the skin heating. The loops provide signals to the user to indicate the presence of conditions under which the treatment is not effective. Such notice enables the user to correct the treatment parameters. All of these features, or the inclusion of a subset of the described features, when incorporated into an embodiment make apparatus 100 ideal for personal use in residential apartment conditions or the like.

Generally, the user may use and operate apparatus 100 or apparatus 250 according to the present method for skin rejuvenation, collagen remodeling and contraction, skin tightening, wrinkle treatment, subcutaneous tissue treatment, cellulite treatment, pore size reduction, skin texture and tone improvement, acne treatment and hair removal.

The method of skin treatment presented may be further enhanced by applying red and infrared radiation generated by lamp 144 (FIGS. 2 and 6) to the surface of the treated segment of the skin 172. This allows treatment of such skin targets as vascular lesions, varicose veins, acne, and mole marks. The optical energy of the lamp or similar optical energy source may have a value of 1 W to 10 W and be applied for a time similar to that of RF application. Actually, simultaneous treatment of skin and skin surface may have mutually beneficial effects. It reduces the risk of adverse effects associated with light only based treatment, and use of RF energy is advantageous in treating most skin types since this form of energy is not sensitive to skin pigmentation.

The skin post-treatment process includes at least gel removal from the skin, cleaning the skin surface treated and if necessary application of a moisturizing cream to reduce post treatment effects.

A number of embodiments have been described. Nevertheless, it will be understood that various modifications may be made without departing from the spirit and scope of the method. Accordingly, other embodiments are within the scope of the following claims:

What is claimed is:

1. An apparatus for personal skin treatment, said apparatus comprising:
   a) an applicator with at least one pair of electrodes mounted on the distal end of the applicator, said electrodes configured to apply an RF voltage to a subject skin; and
   b) an RF voltage generator configured to supply said electrodes with the RF voltage, said RF voltage generator supplying RF voltage in a manner selected from a group of manners consisting of:
      i) a zero potential at one of the electrodes and a maximum potential relative to a ground on the other electrode of the at least one pair of electrodes;
      ii) a minimum potential in the middle between the electrodes of the at least one pair of electrodes, regardless of the potential with respect to the ground-earth; and
      iii) a zero potential in the middle of the span of the electrodes of the at least one pair of electrodes with respect to the ground.

2. The apparatus according to claim 1, further comprising a source of light and a broad band optical filter transmitting red and infrared radiation mounted on the distal end of the applicator with said source of light arranged between said electrodes and illuminating the skin segment between said electrodes through said filter.

3. The apparatus according to claim 2, wherein said electrode is an elongated body with width to length ratio of at least 1:5, mounted on the optical filter.

4. The electrodes according to claim 1, wherein said electrodes are at least one of a group of electrodes consisting of a solid electrode, flexible electrode, or an electrode having a surface relief, and wherein at least one of the electrodes has a built-in thermocouple.

5. The apparatus to claim 2, wherein said source of light is at least one of a group consisting of an incandescent lamp, a lamp optimized for emission of red and infrared radiation and a reflector, or at least one LED.

6. The apparatus according to claim 1, wherein said applicator includes a magnetic or a ferromagnetic insert.

7. The apparatus according to claim 1, further comprising a gel dispenser.

8. The apparatus according to claim 1, further comprising at least one of a group of sensors consisting of a thermocouple, a thermistor, and an accelerometer.

9. The apparatus according to claim 1, further comprising a docking stand that receives said applicator, said stand incorporating:
   a) at least an RF voltage generator;
   b) a magnetic or a ferromagnetic insert; and
   c) an operation indicator.

10. An apparatus for personal skin treatment, said apparatus comprising:
    (a) an applicator with a body a portion of which has been adapted for mounting of at least a pair of electrodes adapted to apply RF energy to a segment of subject skin;
    (b) a docking stand for said applicator, said stand incorporating at least an RF energy generator configured to providing the RF energy to said electrodes and a permanent magnet or a ferromagnetic material adapted to hold the applicator.

11. The apparatus according to claim 10, further comprising an accelerometer.

12. The apparatus according to claim 10, wherein the docking stand further comprises:
    a) at least an RF voltage generator; and
    b) a stand operation indicator of second color.

13. The apparatus according to claim 8, wherein the thermistor is one of a group of thermistors consisting of thermistors embedded into one or more electrodes, or into a standalone probe being in contact with the treated skin segment.

* * * * *